United States Patent
Al-Moniee et al.

(10) Patent No.: US 10,571,401 B2
(45) Date of Patent: Feb. 25, 2020

(54) SENSOR FOR MONITORING FOR THE PRESENCE AND MEASUREMENT OF AQUEOUS ALDEHYDE BIOCIDES

(71) Applicant: Saudi Arabian Oil Company, Dhahran (SA)

(72) Inventors: Mohammed A. Al-Moniee, Dhahran (SA); Naim Akmal, Dhahran (SA); Peter Frank Sanders, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 218 days.

(21) Appl. No.: 15/696,966

(22) Filed: Sep. 6, 2017

(65) Prior Publication Data

US 2017/0363544 A1    Dec. 21, 2017

Related U.S. Application Data

(62) Division of application No. 14/254,445, filed on Apr. 16, 2014, now Pat. No. 9,772,287.

(51) Int. Cl.
| | | |
|---|---|---|
| *G01N 21/64* | (2006.01) | |
| *G01N 33/18* | (2006.01) | |
| *G01N 21/77* | (2006.01) | |

(52) U.S. Cl.
CPC ....... *G01N 21/6486* (2013.01); *G01N 21/643* (2013.01); *G01N 21/77* (2013.01); *G01N 33/18* (2013.01); *G01N 33/1826* (2013.01); *G01N 2021/7786* (2013.01); *G01N 2033/184* (2013.01); *G01N 2201/061* (2013.01); *Y02A 20/206* (2018.01)

(58) Field of Classification Search
None
See application file for complete search history.

(56) References Cited

U.S. PATENT DOCUMENTS

| | | |
|---|---|---|
| 4,438,206 A | 3/1984 | Nakajima et al. |
| 5,702,684 A | 12/1997 | McCoy et al. |
| 2008/0220534 A1 | 9/2008 | Paolacci et al. |
| 2012/0149122 A1 | 6/2012 | Le Calve et al. |

OTHER PUBLICATIONS

Li et al., "Flow injection spectrofluometric determination of trace amounts of formaldehyde in water after derivatization with acetoacetanilide", TALANTA (2007), vol. 72, No. 5, pp. 1675-1680.
Sakai et al., "Fluorimetric flow injection analysis of trace amount of formaldehyde in environmental atmosphere with 5,5-dimethylcyclohexane-1,3-dione", TALANTA (2002), vol. 58, No. 6, pp. 1271-1278.
Al-Moniee et al., "Development of Detection Techniques for Monitoring and Optimizing Biocide Dosing in Seawater Flooding Systems", Proceedings of the 2013 International Petroleum Technology Conference, (Mar. 26, 2013), pp. 1-13.
Sawicki et al., "Spectrophotofluorimetric Determination of Aldehydes with Dimedone and Other Reagants", 1968, Microchimica Acta, vol. 56, Issue 1, pp. 148-159.
International Search Report and Written Opinion dated Jun. 30, 2015 in International Patent Application PCT/US2015/026081.

*Primary Examiner* — Paul S Hyun
(74) *Attorney, Agent, or Firm* — Abelman, Frayne & Schwab

(57) ABSTRACT

An analytical system and method for periodically monitoring an injection water distribution pipeline for the presence and concentration of formaldehyde or other aldehyde-functional biocide includes pumps, one of which provides a predetermined volume of injection water drawn from the pipeline at a sampling point and another of which provides a predetermined volume of a reagent, preferably a buffered solution of dimedone, from a reagent storage vessel, wherein the injection water and reagent are mixed and then heated in a chamber to a predetermined temperature to promote formation of any reaction products. The heated reaction mixture is passed to a detection cell and exposed to light of predetermined wavelength which, in accordance with the Hantzsch reaction, molecules having an aldehyde functional group that reacted with dimedone produce a fluorescence-emitting reaction product, the intensity of which is measured and compared to data previously obtained from standard aldehyde-containing solutions.

25 Claims, 4 Drawing Sheets

SENSOR FOR MONITORING FOR THE PRESENCE AND MEASUREMENT OF AQUEOUS ALDEHYDE BIOCIDES

RELATED APPLICATION

This application is a divisional and claims the benefit of U.S. patent application Ser. No. 14/254,445 filed Apr. 16, 2014, the disclosure of which is hereby incorporated by reference.

FIELD OF THE INVENTION

This invention relates to the continuous monitoring for the presence and measurement of the concentration of aldehyde biocides in aqueous systems.

BACKGROUND OF THE INVENTION

In oil exploration and production fields, seawater is pumped into strategically positioned injection wells to enhance the recovery of oil from the reservoir. The recovery of oil requires injection of water into oil-bearing reservoir rock in order to move the hydrocarbons to a production well where they can be produced to the surface. The length of the pipeline from the source of the water to the oil field where it is to be injected can be thousands of kilometers. The residence time of water in the pipelines can be significant and the likelihood of the presence of conditions that promote bacteria growth is extremely high. The growth of bacteria in the pipeline can be prevented or greatly inhibited by the addition of a biocide at the water intake point that will have the effect of inhibiting bacterial growth throughout the pipeline.

The distribution pipelines normally form a grid to supply water to a number of injection wells in the vicinity of the production wells. Because of the overall length of the pipeline system, a drop in the effective concentration of biocide can occur at the point of use. The reduction in biocide concentration is due to the degradation of the active ingredient(s) present in the biocide formulation. Hence, it is important to know the actual concentration of biocide present in water at the point of use.

Biocides are also commonly added to water used in cooling towers and similar industrial systems to combat growth of bacteria. For most cooling tower installations, the degradation of the biocide is not an issue since the pipelines used with the cooling tower are not of great length; hence the concentration of biocide added remains almost constant throughout the cooling tower system. Generally, the addition of a biocide, or biocides to a distribution pipeline is at the main water intake point. For pipelines, the quantity added at the initial injection point is dependent upon the flow rate of water, ambient pipeline conditions and the length of the pipeline. The customary biocide treatment method for the biocide addition to an injection water stream is not continuous; rather, the biocide is added into the water system periodically on a fixed schedule that has been determined based on experience.

Many commonly used industrial water treatment biocide formulations contain formaldehyde and/or other compounds having an aldehyde functional group as the active ingredient to combat the growth of bacteria. After the addition of a predetermined amount of biocide over a prescribed time period (commonly referred to as a "slug"), a water sample is collected manually at various downstream sampling points and the samples are taken to a laboratory where any of a number of known analytical methods can be used to detect the presence and determine the concentration of any biocide in the sample of injection water. Once the samples have been received, the laboratory generally requires several hours to report the concentration of any biocide present in the water system. This practice is followed on a regular basis and after the addition of biocide into seawater at the point of water intake. This method of analysis is time-consuming and is not always practical at remote locations along the pipeline. Due to the complexity of some water injection networks in large oil fields, including those comprised of remote locations, the water distribution system cannot be effectively monitored by personnel at the sites for treatment and measurement of residual biocide concentration. Additionally, due to the high volumetric flow of water and pipeline length, it is often difficult to precisely determine when the biocide slug will arrive at the water sampling point, leading to a missed opportunity.

The problem addressed by the present invention is the monitoring of biocide in a stream of injection seawater on a continuous basis. Another essential aspect of the problem is to determine the concentration of biocide in the water system at the point of use, and at interim sampling points in real-time, utilizing means capable of determining the presence and also recording the concentration of the active ingredient, e.g., formaldehyde and/or other aldehyde functional groups.

Currently, there is no method or apparatus commercially available for the continuous monitoring for the presence of a biocide in an aqueous medium and no commercially available analyzer system that automatically samples, detects and measures the concentration of aldehyde-functional biocides in seawater injection distribution systems.

There is a need for in-line and real-time sensing devices for continuous monitoring of biocidal chemicals in these geographically extensive and complex water distribution systems. A system in which such test information is recorded and that is able to transmit the data from remote locations to personnel responsible for the system is needed.

SUMMARY OF THE INVENTION

The above problems are resolved and other advantages are provided by the method and analytical system of the present invention, which comprehends an in-line system that includes a sensor and analyzer assembly that continuously monitors for the presence and measures the concentration of any aldehyde-containing biocide detected in injection water streams, and in industrial and waste water streams. The in-line system is equipped with a microprocessor/controller which transmits test data to an offsite control center, allowing for the monitoring of aldehyde-containing biocide in remote pipelines. As used herein, the term "aldehyde-containing biocide" includes a biocidal composition containing formaldehyde and/or one or more aldehyde functional groups that react with dimedone.

An automated system is provided for indicating the presence and concentration of the biocide by incorporating the reaction of aldehyde with dimedone to monitor the seawater injection system for the presence of biocide. The sensor and analyzer assembly includes a combination of flow pumps, an injection valve, a mixer, a heating chamber and an optical detection cell.

The detection of the aldehyde and/or aldehyde functional group utilizes the chemical reaction of a reagent with a biocide that contains an aldehyde group. The primary mechanism for detection is the Hantzsch reaction in which molecules having an aldehyde functional group react with dimedone in the presence of a buffering agent such as ammonium acetate, to produce a reaction product that is fluorescent. The Hantzsch reaction mechanism can be represented as follows:

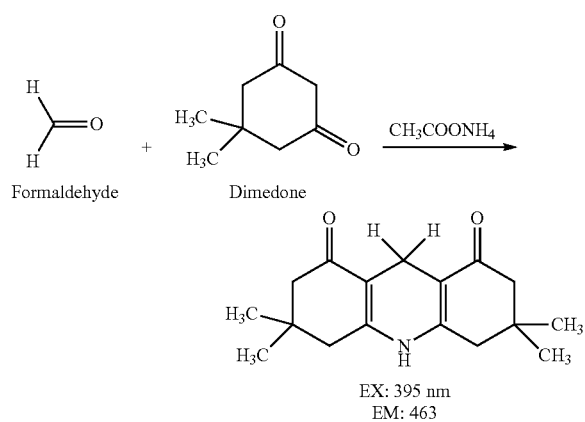

A buffer is preferably added to maintain the pH of the reaction medium at about 4.5. It is possible to use other buffering agents to maintain this pH value.

Although the rate of reaction and formation of the fluorescent product is relatively slow at room temperature, the rate is accelerated by increasing the temperature of the reaction medium. The product formed produces high levels of fluorescence at temperatures in the range of 80° to 90° C.

The reaction between formaldehyde and dimedone differs from the reaction of acetaldehyde or glutraldehyde with dimedone since the reaction products formed may fluoresce at slightly different wavelengths. It has also been found that different aldehyde molecules produce different levels of fluorescence in their reaction with dimedone. When different aldehydes are present in the biocidal system added to the seawater, the detection system requires a calibration curve that is specific for each of the aldehydes.

The purpose of the buffering system is to maintain the pH of the reaction media at about 4.5, because it has been found that the product formed at a pH of approximately 4.5 shows a higher level of fluorescence when other conditions, e.g., temperature, are held constant.

A buffering agent is not required in order for the Hantzsch reaction to proceed, but it is preferable to operate at this pH, particularly in order to more effectively detect the presence of low levels of biocide in seawater and to assure that the reaction goes to completion. The buffer solution helps to maintain the response for the relatively lower concentrations of biocide that may be present in the seawater injection systems.

In the absence of a buffering agent, the reaction is slow and the detection of a biocide in the seawater is also slowed, resulting in very a broad peak. Additionally, the response is not readily reproducible in the absence of a buffer.

In addition to ammonium acetate, another suitable buffer includes a mixture of potassium hydrogen phthalate and sodium hydroxide. The buffer can be added as an aqueous solution. The concentration of the buffer agent can be in the range of a pH of 4.0 to 5.0.

It has been noted that the presence of minerals in the seawater does not affect the response.

In the apparatus of the invention, the aqueous sample that is to be tested for the presence of a biocide with an aldehyde functional group and the dimedone reagent are maintained in separate containers. Predetermined quantities of the aqueous sample and reagent are withdrawn by separate pumps, mixed, and then heated in a vessel or chamber to the desired temperature; thereafter, the heated reaction product is exposed to light from a lamp of predetermined wavelength in a detection cell. The wavelength of the light can range from about 380 nm to 480 nm.

The detection cell can be constructed from readily-available components as a two-part assembly that includes a chamber fitted with a transparent wall or window for receiving the flowing mixture and a second chamber containing the sensor of the optical detection device which is isolated from the liquid containing the reaction product by the transparent wall. The limiting reactant in this reaction scheme is the molecule containing an aldehyde functional group. The signal produced by the optical detection probe is directly proportional to the amount of reaction product formed in the reaction of the aldehyde molecule and dimedone, which in turn is directly proportional to the amount of aldehyde present in the sample being tested.

Different manufacturers and suppliers of the biocidal water treatment compositions utilize different types of aldehydes, including formaldehyde, acetaldehyde and glutraldehyde. The method and system of the invention are capable of detecting the presence of any molecule containing a —CHO functional group. The sensor system is first calibrated by testing aqueous samples containing predetermined known concentrations of an aldehyde. Once calibrated, the sensor can be utilized to monitor for the presence of the known aldehyde and to measure the concentration of any known aldehyde in the aqueous samples withdrawn from the pipeline sampling points. The sensor system is preferably automated for analysis of samples that are periodically withdrawn from a remote pipeline, the principal limitation of the system being the availability of a supply of the dimedone reagent and knowledge of the type of aldehyde added to the seawater.

The advantages provided by the present invention include:

a. enhancing the reliability of an established injection water treatment program by the timely detection of biocide residuals and adjusting upstream operating parameters and conditions accordingly to provide adequate control of any bacterial activity in the system;

b. minimizing potentially serious and costly downhole bacterial growth problems resulting from the depletion of biocide in a geographically extensive seawater distribution system and enhancing the effectiveness of bacterial control and the water quality in remote areas; and c. avoiding the addition of an unnecessary excess of biocide to the injection water system thereby achieving cost savings and reducing the amount of biocide used.

BRIEF DESCRIPTION OF THE DRAWINGS

The invention will be described in further detail below and with reference to the attached drawings in which the same or similar elements are referred to by the same number, and where.

DETAILED DESCRIPTION OF THE INVENTION

Figure 1:
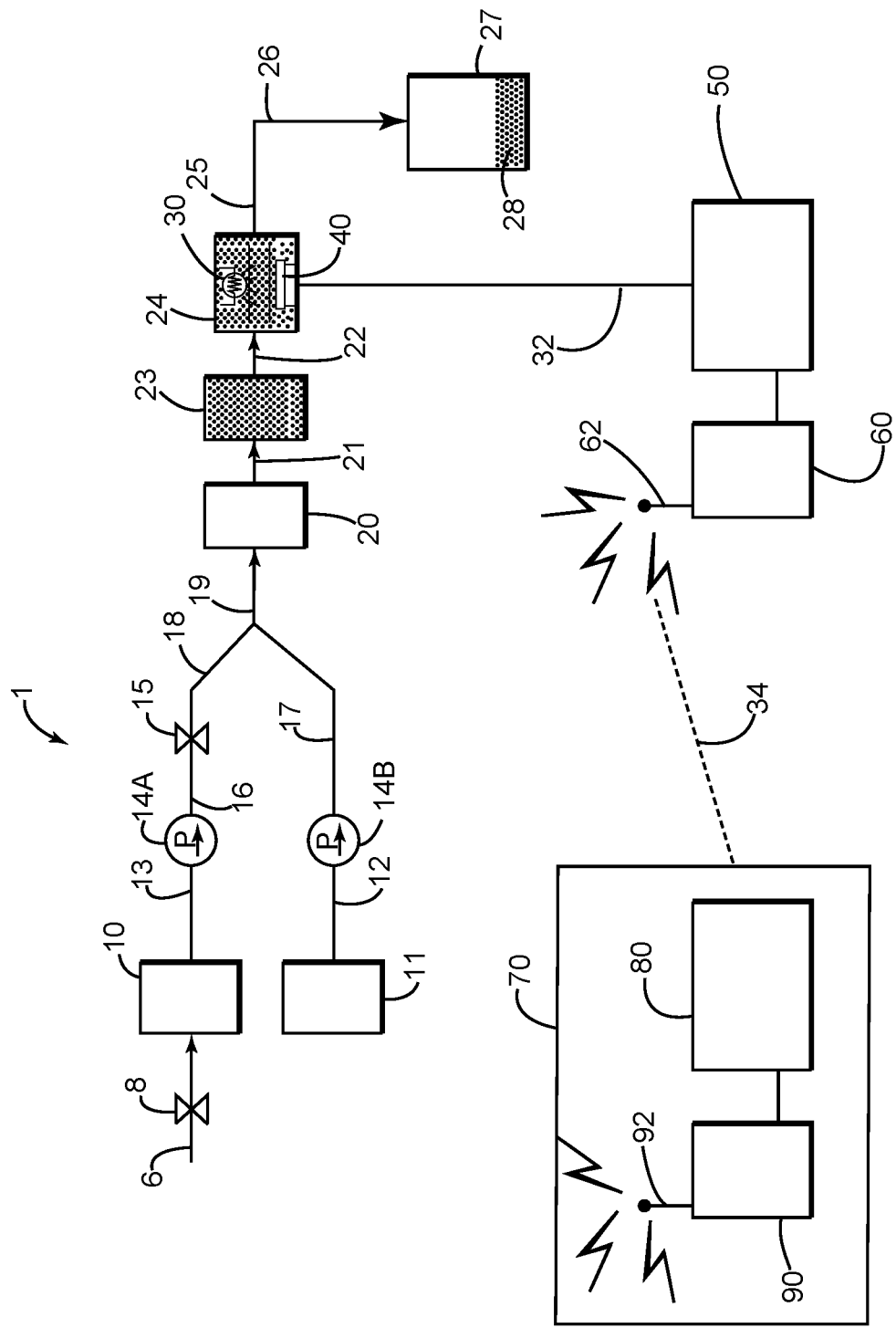
FIG. 1 is a schematic diagram of a sensor/analyzer system that includes flow pumps, an injector, a loop mixing chamber, a heater module, an optical sensing device for continuous and regular monitoring for the presence of an aldehyde-containing biocide in an aqueous system, and a microprocessor/controller equipped with a transmitter and antenna used to transmit data from the optical sensing device to an offsite control center that is equipped with a receiver/transmitter and antenna to receive the transmitted data and that is linked to a separate microprocessor/controller.

As noted above, the system and method of the present invention are directed to a chemical reaction product-based analyzer for regularly monitoring the flowing stream of injection water for the presence and concentration of formaldehyde and/or other aldehyde functional biocide(s). The system is configured and operated to monitor for the presence of an aldehyde-containing biocide in an aqueous medium without human intervention. The automated system is based on the reaction of the aldehyde and reagent which are mixed and heated to a predetermined temperature to produce an optically detectable fluorescence when exposed to a known wavelength of light.

The analyzer includes two pumps, one of which provides a predetermined volume of injection water drawn from the pipeline at a sampling point and the other delivers the reagent, e.g., dimedone, from a reagent storage vessel. In a preferred embodiment, peristaltic pumps are used for delivery of the liquids at a constant rate. It is also preferred to mix the buffer solution with the dimedone reagent so that the buffer solution is delivered as a single stream by the pump. The output from each of the pumps is introduced into a mixing chamber to provide a uniform mixture and then heated to a predetermined temperature, as will be explained in more detail below. The mixing and heating steps can be combined in a single vessel. Heating the reactant produces a chemical product which fluoresces at a known wavelength. The fluorescent liquid is passed through a detection cell equipped with a fiberoptic pick-up probe that receives the light waves. The volume of injection water containing the reacted aldehyde moiety is controlled using an injection loop downstream of the flow pump. Sufficient time is allocated to insure that all the aldehyde present in the injection loop has reacted with an excess of dimedone to produce the fluorescent reaction product. The loop accommodates all of the seawater sample mixed with the buffered dimedone solution. The amount of aldehyde in the seawater is the limiting reactant so that all the biocide that may be present in the seawater completely reacts with dimedone reagent.

The analyzer is pre-calibrated using a known concentration of an aldehyde in a volume of liquid equivalent to the volumetric capacity of the loop. The response is preferably recorded in the form of the total area under the produced peak. Following calibration, the analyzer is placed in the sample analysis mode. The software used in the system is based on a generic product such as a visual basic program used in conjunction with LabVIEW software. The program can be prepared by a programmer of ordinary competence.

The detection cell is calibrated by reacting a predetermined concentration of aldehyde with the reagent and the intensity of the fluorescence produced is measured by optical means and converted by the software into a graphic display and/or tabular data. The area under the peak is measured and a response factor is calculated. A plurality of samples over an appropriate range of varying concentrations that can be determined by experience are preferably prepared to establish the factors. For example, the calibration curve is obtained by preparing a known concentration of formaldehyde in water and its value is kept close to the experiential levels of formaldehyde present in the seawater injection system. Two different sample standards can be prepared; one at about 200 ppm of formaldehyde in water and the other at about 700 ppm to cover the high and low ranges of the desired concentration of biocide present in the seawater injection system. In the case of a water sample containing the biocide reaction product, a similar peak is generated. The area under the peak and the response factor determined in the calibration step is used to calculate the amount of biocide present in the sample of injection water drawn from the pipeline.

In the practice of the method of the invention, the sample of water containing an aldehyde functional group reacts with the dimedone reagent to produce molecules which fluoresce at the wavelength of the light source in the detection cell. The emitted light is gathered in the fiber optic probe and transmitted to a sensor in the optical detector. The signal from the optical detector is transmitted to a suitably programmed microprocessor known in the art. The output signal from the microprocessor operates a graphic plotter and is translated into a peak from which the concentration of aldehyde present in the flowing sample is calculated. The data is transmitted to an offsite control center where it is displayed on a monitor and/or printed for review by a technician. All data is entered for retention in an associated suitable storage medium. In the event that separate analyzers are utilized for many different sampling points in the distribution system, it is preferred that a dedicated set of calibration curves be developed and used with each analyzer. The detection cell can be constructed from commercially available parts and was designed specifically for this new application.

The optical detection cell operates on the basic principle of the Beer-Lambert Law which states that there is a logarithmic relationship between the transmission, or transmissivity, T, of light through a substance and the product of the absorption coefficient of the substance, $\alpha$, and the distance the light travels through material, i.e., the path length, $l$. The absorption coefficient can, in turn, be written as a product of either a molar absorptivity, or extinction coefficient of the absorber, $\varepsilon$, and the molar concentration, c, of the absorbing species in the material, or an absorption cross-section, $\sigma$, and the density $N'$ of absorbers.

The amount of sample selected for predetermined injection is based on the volume of the sample loop. A loop having a relatively larger sample volume will produce a stronger signal and will be capable of accurately measuring relatively lower concentrations of an aldehyde biocide in the aqueous sample by producing a larger area under the peak. It will be understood that once the analyzer is calibrated for one, but preferably a plurality of specific calibration concentrations of aldehyde in the water sample, the same volumetric loop size is maintained for the analysis of subsequent test samples. The loop/detection cell is flushed out with seawater between sample tests to eliminate any fluorescent reaction product and dimedone carry-over from the previous analysis and to prevent blocking of the sample lines with salt deposits from the seawater.

The operation of the analyzer is preferably controlled by a suitably programmed microprocessor so that it can operate without human intervention after it has been installed in the field. In a preferred mode of the practice of the invention, a plurality of analyzers are installed along the water injection distribution system in the field for substantially continuous monitoring for the presence and determination of the concentration of biocide at different locations in the pipeline system. The microprocessor control system can utilize dedicated software that operates the analyzer in three modes, i.e., (a) continuous or frequent mode; (b) a slug or intermittent detection mode; and (c) calibration mode. It will be understood that the use of the term "continuous" is relative and that the time between tests is limited by the time required to initiate sampling, process the sample, and collect the data from any fluorescence detected. However, when compared to prior art methods and procedures which required collected samples to be carried to a laboratory, the present method is aptly characterized as capable of substantially continuous monitoring with the reporting of results in real time.

Example of Analyzer Operational Mode

The following sequence describes an embodiment for automated operation of the system. The dedicated software initiates sampling of the pipeline in the intermittent or slug detection mode. Sampling is initiated based on a predetermined schedule, e.g., once every hour, and an analysis is performed. The frequency of injection can be changed based upon experience with the particular system, location and number of sampling points, the number of injections required and the volume of the reagent reservoir available for use in the analyzer. If no biocide reaction product is detected during the analysis, the sampling continues in the intermittent mode. If a biocide reaction product peak is detected, the software switches to sample analysis mode for the next run. In sample analysis mode, a sample injection occurs every seven minutes for as long as some product is detected. The biocide concentration is determined by a factor provided by user input. The compositional information is of a particular biocide provided by the supplier in the MSDS or other commercial literature or product labels. The concentration of formaldehyde or other aldehyde-containing compounds present in each formulated product can vary based on the manufacturer or supplier specification. If no biocide peak is detected following a sample analysis, the software returns sampling to the plug flow or intermittent detection mode. This mode of operation minimizes the use of reagent when no aldehyde group has been detected.

The operation of the analyzer is not affected by temperature variation due to the fact that the chemical reaction proceeds at a predetermined temperature that is much higher than ambient temperatures so that even significant variations in ambient temperature, e.g., in desert and arctic environments, will have little or no effect on the outcome and the accuracy of the analysis. This represents a significant advance in the art of providing real-time results from remote locations with minimal human intervention.

In a preferred embodiment, the analyzer is used in conjunction with a solar powered energy source connected to one or more storage batteries capable of providing sufficient electrical power to operate the microprocessor, pumps and heating system in locations that are remote from an established power grid.

The analyzer is initially calibrated using known concentrations of aldehyde-containing biocides that produce a fluorescence, the magnitude or intensity of which is detected by the optical sensor and converted to a corresponding data entry that is stored in the memory of the microprocessor with the sample concentration and other related information for reference during subsequent injection water sample testing. If changes are made to the type or supplier of the commercial biocides, the new products should be subjected to the same calibration steps and the resulting data entered into the memory of the microprocessor associated with the analyzer for reference during injector water sample testing.

The apparatus is calibrated in this way using varying concentrations of different biocides of the type that are used in the injection water distribution system. As will be understood by those of skill in the art, this calibration data set can be used with an apparatus that is manufactured using the same components and a consistent design. Any changes in the configuration of the components, optical sensor and the like may necessitate the preparation of a new set of calibration data for storage and reference in the memory of the associate microprocessor.

Description of a Preferred Embodiment

Referring now to FIG. 1, the biocide analyzer system (1) includes injection water sampling tube (6) which is in fluid communication with a sampling point in a section of an injection water distribution system. Tube (6) delivers injection water containing biocide through injection water valve (8) to the sample or calibration solution reservoir (10). It will be understood that the sampling procedure is also applicable to the preparation of the calibration data from known concentrations of commercial biocides of the type customarily used in the injection seawater system.

A sample pump (14A) is connected to sample or calibration reservoir (10) by sample delivery conduit (13) and a predetermined quantity of the injection water sample that is to be tested for biocide is injected into the system through injection valve (15). Reagent from reagent storage reservoir (11) is carried via conduit (12) to reagent pump (14) and downstream conduits (17, 19) to be mixed with sample water which may contain biocide in mixing vessel (20). The mixed sample is transferred via transfer conduit (20) to the heating vessel (23) where the sample is heated to a predetermined temperature at which the rate of reaction is accelerated in order to increase the rate of formation of any of the fluorescent reaction product. After a predetermined period of time that is sufficient to substantially complete the reaction of any aldehyde present, the reaction mixture is introduced via heated sample conduit (22) into optical detection cell (24), where it is exposed to the light of the lamp (30) and any fluorescence of the reaction mixture (28) is detected and measured by sensor (40). After the measurement has been completed and recorded, the liquid (28) is passed through discharge conduit (26) and collected as waste in a reactant product storage chamber (27).

The fluorescence intensity measurements are recorded by the programmed microprocessor/controller (50), which receives the measurements via conduit (32), and then transmitted in real time to an offsite control center (70) via transmitter (60) and antenna (62). The offsite control center (70), utilizing a microprocessor (80) equipped with a transmitter (90) and antenna (92), receives the real time fluorescence intensity measurements via signal (34). The fluorescence measurements are analyzed at offsite control center (70) and any necessary adjustments to the biocide treatment process can be determined with the aid of microprocessor/ controller (80) and communicated to field personnel to adjust the biocide addition schedule.

Figure 2:
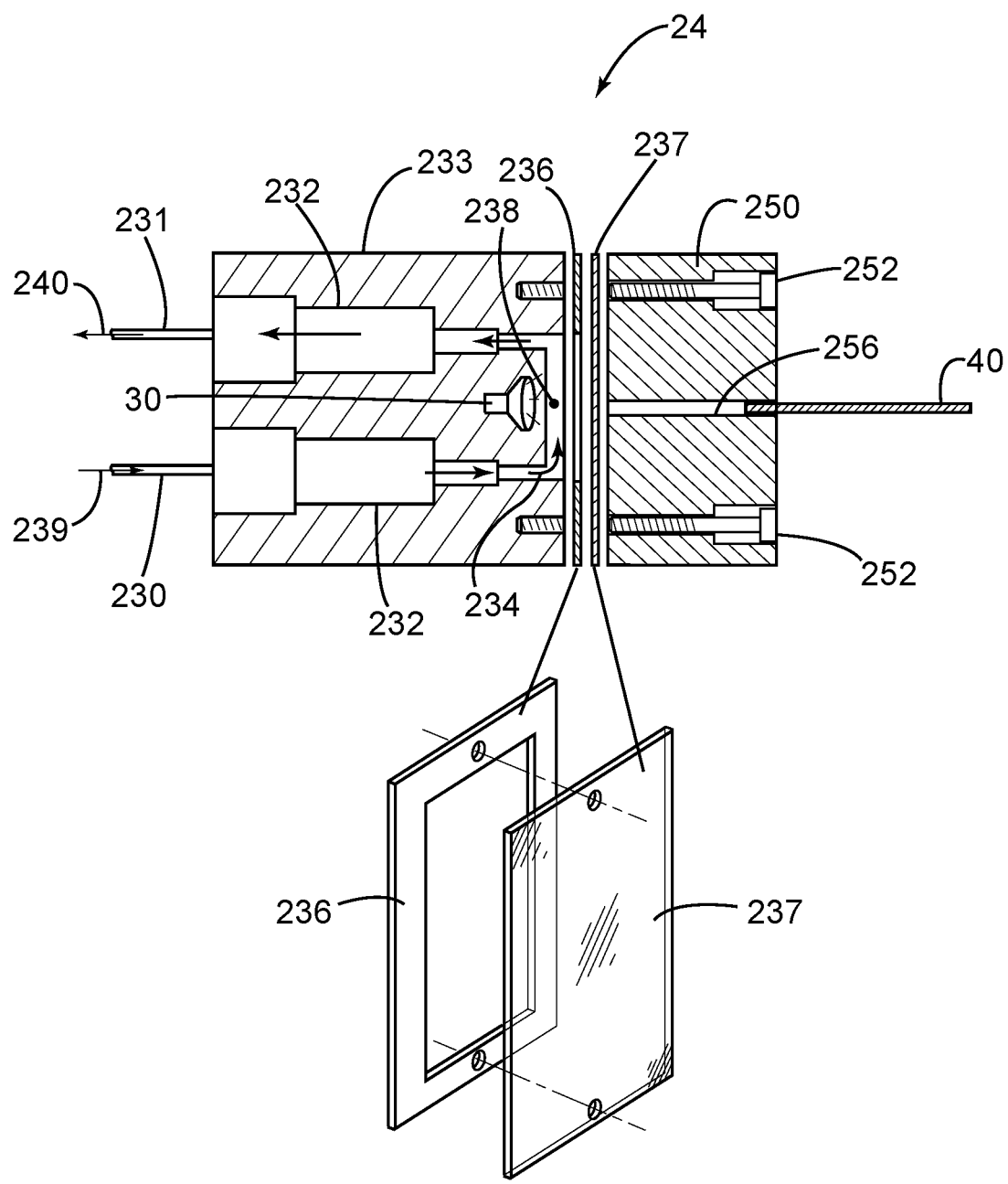
FIG. 2 is a schematic diagram of an optical detection cell suitable for use in the analyzer system of FIG. 1 to detect any fluorescence emanating from a biocide reaction product.

The optical measurement cell (24) is described in more detail with reference to FIG. 2, and in the embodiment illustrated is comprised of a flow cell (233) and a sensor portion (250). The mixture of reaction product, liquid sample and excess reagent (239) enters the flow cell (233) through an inlet (230) and fitting (232). The liquid is passed through chamber (234) where it is exposed to the light emitted by the lamp (30). A silicone spacer (236) is placed over the detection cell (250). The liquid is retained in the chamber by a sheet or web (237) of chemical-resistant transparent plastic material. The sensor-receiving portion (250) of the detection cell is secured to the flow cell (233) with suitable fasteners (252). The liquid (239) flows out of the flow cell through fitting (232) and outlet (231). The flow cell (233) is constructed of a chemical-resistant material such as polytetrafluoro ethylene (PTFE), and the sensor portion (250) is constructed of either PEEK or PTFE. The fiberoptic probe (40) is inserted in sensor channel (256) with its receptor end in position opposite the flow line (238), which has been exposed to the light of the lamp (30) to detect any fluorescence resulting from the above-described reaction. Following each test, the loop is flushed with seawater to prevent carry-over of any reagent and to prevent the build-up of solid salt minerals.

Figure 3:
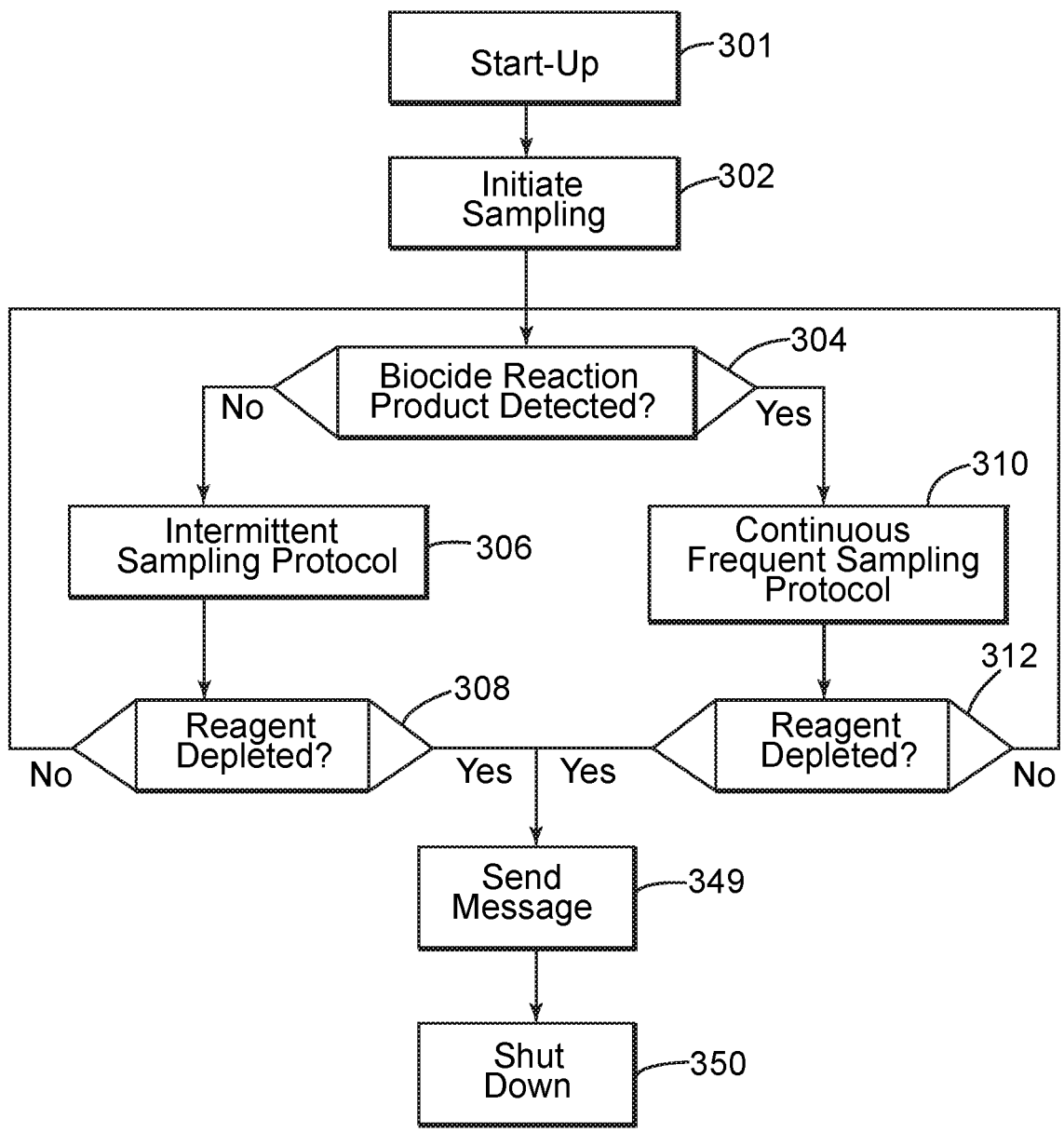
FIG. 3 is a process flow chart of the automated sampling process in which the system analyzes samples on a substantially continuous basis at prescribed intervals when biocide is present in the sample and changes to a standby mode with less frequent sampling and analysis when the biocidal compound is no longer detected.

FIG. 3 is a process flow chart of the method of operation. Following installation of the analyzer at a sampling point, the start-up procedures (301) include the filling of the reagent storage vessel, confirming the charged status of the storage battery and operability of the solar collection device, proper functioning of the pumps, mixing device and heater, and installation of the software, including storage in its associated memory of the calibration data that will be used to determine the concentration of the aldehyde reaction product for actual seawater samples during the tests. In the event that an error or malfunction is detected, the microprocessor transmits an alert message or alarm to the maintenance personnel for appropriate action.

Sampling is initiated (302) either by a manual switch actuated by personnel at the site or remotely via transmission of a signal to a receiver/transmitter associated with the analyzer. Once activated, the analyzer operates in a substantially continuous mode requiring no human intervention.

In a preferred embodiment, the system checks for the presence of adequate reagent to continue the testing protocol (312). This step can also include generation of a warning signal indicating a predetermined low level of reagent in the storage vessel. In either of these events, e.g., low or no reagent detected, a signal will be transmitted to the appropriate maintenance personnel to alert them to the condition. Where there is adequate reagent to proceed, the system checks to see if the aldehyde reaction product was detected in the last sampling (304) and if so, a peak is produced. Once the peak is produced, its detection causes a signal to be generated in the microprocessor. The analyzer continues to run and analyze samples on a predetermined continuous frequent sampling protocol (310), e.g., every five to ten minutes until there is no biocide reaction product detected. In the event that no biocide reaction product is detected (304), the analyzer proceeds to the intermittent sampling protocol (306), e.g., sampling every 60 minutes in order to reduce consumption of reagent. Again, the availability of reagent is checked (308), and if sufficient reagent is available for continued testing, the intermittent sampling protocol continues to check for the presence of biocide reaction product (304). The intermittent sampling protocol continues so long as there is no reaction product detected; once reaction product is detected, the frequent sampling protocol cycle as described above is initiated and continues until no fluorescence from a reaction product is detected, after which the system returns to the intermittent sampling protocol.

In both modes of operation, the condition of low or no available reagent results in an appropriate signal being sent to bring this condition to the attention of maintenance personnel (349) and thereafter the system shuts down (350) pending appropriate maintenance actions. In a further preferred embodiment, basic system checks are routinely performed to confirm that the various elements are functioning within predetermined operational parameters. This would include the determination of battery status, power received from the solar energy collection device, load measurements on the pumps during operation, and the like. Appropriate action must also be taken in setting up the apparatus in order to account for special environmental conditions, e.g., sand storms in remote desert locations and snow in arctic areas that will interfere with the solar energy collection device. Procedures and means for dealing with these environmental issues are known and available for use with the system of the invention and need not be elaborated here.

Figure 4:
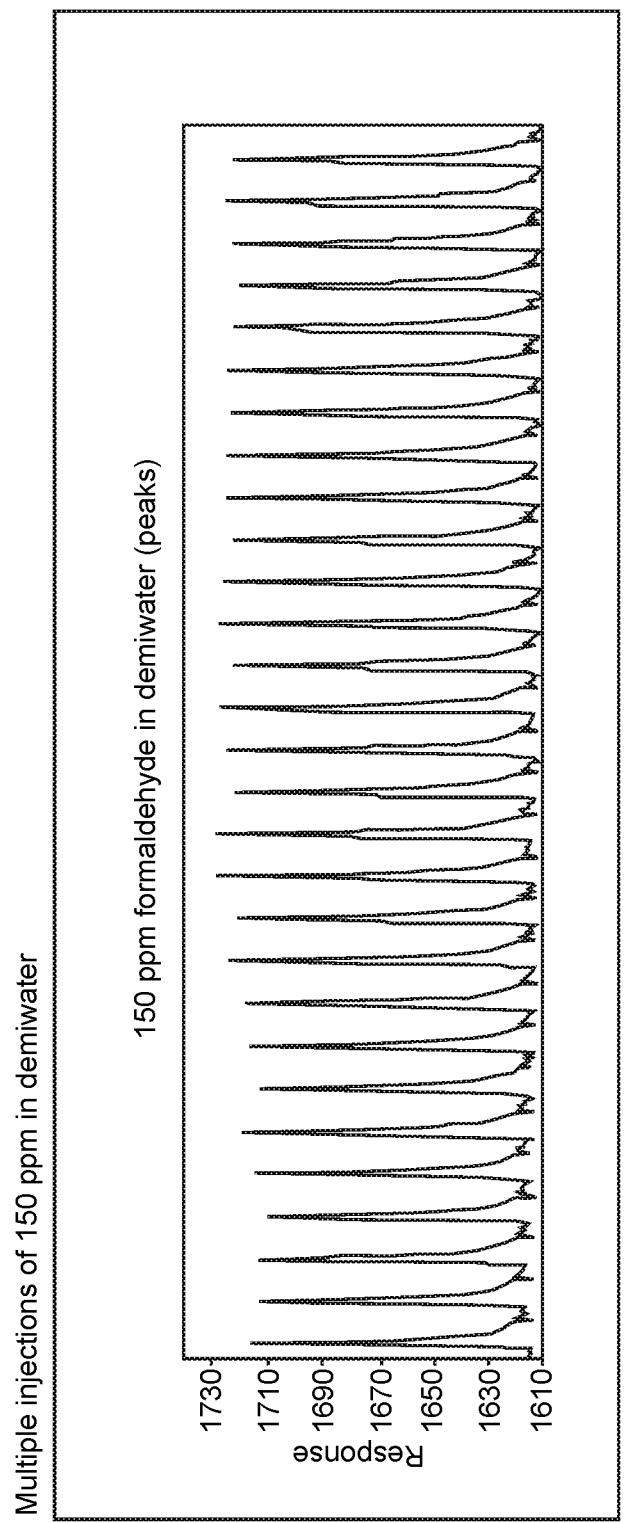
FIG. 4 graphically depicts a peak-by-peak response to the presence of a biocide in samples taken from a seawater injection system feedstream.

FIG. 4 is a graphic representation of multiple injection responses for 150 ppm of formaldehyde in demineralized water. The response plotted is representative of a biocide present as a slug in the seawater injection system. The graph depicts the continuous response of the analyzer for the presence of the biocide. The x-axis represents the number of injections and the y-axis is the detector response and is in arbitrary units. The baseline at 1610 is an arbitrary number associated with the particular detector cell employed in this series of tests. While the baseline is arbitrary, it should be stable from one injection to another since a stable baseline for multiple injections indicates that the analyzer is operating properly.

This invention can be applied to a plurality of remote sampling points and provides a sample handling system in which data can be collected, stored and most importantly, transmitted electronically to the engineers and technicians responsible for maintaining the seawater treatment system. The following detailed steps illustrate the method of operation of an embodiment of the present invention:

1. A freshly prepared biocide standard sampling line is connected to the inlet of the analyzer. A built-in peristaltic pump moves water to fill the injection loop and remaining water is discharged as waste. A second pump continuously introduces the reagent through a second line. Reagent and water containing biocide are metered into a mixing vessel and thereafter the mixed solution is heated to approximately 90° C. The heater is designed to heat the specific volume of the vessel to a temperature for optimum reaction conditions and the mixing and heating steps can be performed in a single vessel. In an illustrative embodiment shown in FIG. 2, the reaction vessel is constructed from a polyether ether ketone (PEEK) cylinder that contains in its core a 130 cm coil of PTFE tubing having an internal diameter of 0.7 mm and an internal volume of 0.5 ml. This reaction coil is enclosed in a heat-resistant isolation jacket formed from meta-aramid paper (tradename NOMEX) and polyimide tape (tradename KAPTON). On the outside of this jacket is coiled 325 cm of resistive wire (Mn—Ni, 11.8 Ω/m, 80 micron core from AB Kanthal, Sweden). The power rating of this resistive heater is 15 W at 24 VDC. The coiled jacket is secured with polymide tape and inserted into the PEEK cylinder housing. The completed assembly is insulated with rigid polyurethane foam.

The resistance heating coil of the reaction chamber is controlled by a commercially available proportional-integral-derivative (PID) temperature controller that is connected to the heater coil through a power metal-oxide semiconduction field-effect transistor (MOSFET) circuit which is driven by the SSR output of the PID. The temperature measurement is performed with a resistance thermometer, such as a PT100 probe, that is connected to the PID temperature input.

The heated mixture is introduced into the optical detection cell. In the optical cell, any fluorescence produced by the exposure to light source is detected, and if present, the intensity of the fluorescence is measured; a comparison of the test sample values is made to the values of calibration samples stored in the memory associated with the analyzer's microprocessor; the concentration of aldehyde in the test sample is then recorded. The concentration of the reaction product is directly related to the concentration of the aldehyde functional group of the biocide.

2. The value of the area under the peak is calculated and recorded by the processor and a response factor is automatically calculated. A log of readings is entered in the associated memory device as a permanent record.
3. The injection seawater line containing biocide is connected to the sample inlet. Water is allowed to flow through the injection loop and the procedure of step 1 is repeated to record the value of the peak area. The peak area value and the response factor as was calculated in step 2 are recorded for the seawater sample.
4. The peak area and the response factor calculated in step 2 are used to calculate the amount of biocide present in water based on the sample peak area value.
5. Further, the seawater samples are periodically admitted for analysis, e.g., every 7 to 10 minutes for as long as biocide is detected in the samples. This is referred to as the continuous or frequent sampling mode.
6. If no biocide is detected in a seawater sample, the system processor resets to sampling of the injection water pipeline at sixty-minute intervals. This is referred to as the intermittent detection or monitoring mode.

The analyzer system is capable of measuring 20 to 2000 ppm of biocide that contains aldehyde-based active ingredients present in an aqueous system, e.g., biocidal-treated seawater.

The following analytical data was obtained from field studies using the method and apparatus of the invention described above. The readings in Table 1 are parts per million (ppm) of a residual biocide identified as product TK-1415 as detected by the aldehyde analyzer in samples of treated seawater intended for use in injection wells.

TABLE 1

| SENSOR READINGS (Biocide TK-1415) | |
| --- | --- |
| TIME (hr/min) | CONC. (ppm) |
| 14:50 | 198 |
| 16:01 | 1412 |
| 16:12 | 1514 |
| 16:22 | 1452 |
| 16:32 | 1385 |
| 16:42 | 1350 |
| 16:52 | 1249 |

TABLE 1-continued

| SENSOR READINGS (Biocide TK-1415) | |
| --- | --- |
| TIME (hr/min) | CONC. (ppm) |
| 17:13 | 789 |
| 17:23 | 1210 |
| 16:33 | 196 |

The data in Table 2 are readings taken at varying time intervals for a different aldehyde-based biocide identified as product TK-1420. These data are for two different formulations of biocidal compositions containing different amounts of the active ingredient.

TABLE 2

| SENSOR READINGS (Biocide TK1420) | | |
| --- | --- | --- |
| TIME | CONC. | REMARKS |
| 05:37 PM | 141 | |
| 07:19 PM | 347 | |
| 07:29 PM | 210 | |
| 07:39 PM | 144 | |
| 09:21 PM | 147 | |
| 09:42 PM | 171 | |
| 10:53 PM | 212 | |
| 12:15 AM | 278 | |
| 12:25 AM | 195 | |
| 01:16 AM | 231 | |
| 01:26 AM | 223 | |
| 01:47 AM | 166 | |
| 02:48 AM | 203 | |
| 03:29 AM | 237 | |
| 04:50 AM | 194 | |
| 05:01 PM | 207 | |
| 06:58 PM | 301 | |
| 12:35 AM | 168 | |
| 03:38 AM | 213 | |
| 05:00 AM | 200 | |
| 07:13 AM | 175 | |

From the above description, it will be understood that the analyzer of the invention provides a system and method to detect the presence and the concentration of an aldehyde-based biocide in a water system on an essentially continuous sampling basis. The analyzer functions independently of the temperature, flow rate and pressure of the stream being sampled. The chemical reaction between the active aldehyde ingredient present in the biocide and the reagent produces a fluorescent molecule at the operating temperatures. The mode of operation of the analyzer is based on measurement logic. In order to maximize the time for the uninterrupted operation of the analyzer in the field over an extended period of time, it functions to take samples for frequent testing only when the biocide is likely to be present in the flowing stream of water. If no biocide is detected in water, the analyzer decreases the frequency of sampling and testing. This feature allows conservation of stored reagent in the analyzer system and prolongs the time over which the system can operate before reagent must be replenished. The data is routinely transmitted to operations personnel in real time who can then take appropriate steps to maintain the level of chemical addition at the intake point that is necessary to meet the requirements established for the use of the injection water in the field.

The system and method of the invention have been described in detail above an in the attached drawings; however, modifications will be apparent to those of ordinary skill in the art from this description and the scope of the invention is to be determined by the claims that follow.

The invention claimed is:

1. An analytical system for real-time detection, measurement, and recording of the concentration of any aqueous aldehyde-based biocidal compounds present in an aqueous solution flowing in a conduit at a sampling point, the system comprising:
   a sample delivery valve having an inlet in fluid communication with the conduit at the sampling point and an outlet connected to an aqueous sample storage vessel for delivering a sample of the aqueous solution to the aqueous sample storage vessel;
   a mixing vessel;
   an aqueous sample metering pump having an inlet in fluid communication with the aqueous sample storage vessel and an outlet in fluid communication with the mixing vessel for delivering a predetermined volume of the aqueous solution to the mixing vessel;
   a reagent metering pump having an inlet in fluid communication with a reagent storage vessel containing a reagent and an outlet in fluid communication with the mixing vessel for delivering a predetermined volume of the reagent to the mixing vessel, the reagent comprising a solution of dimedone and a buffering agent in an amount necessary to maintain the pH of the reagent in a range of 4.0 to 5.0;
   a heating vessel in fluid communication with the mixing vessel for receiving and heating a reaction mixture of the reagent and the sample and any reaction product to a predetermined temperature;
   an optical detection cell in fluid communication with the heating vessel for receiving and circulating the heated reaction mixture and any reaction product, the optical detection cell constructed as a two-part assembly comprising a flow cell and a light sensor; and
   a microprocessor and associated memory connected to the light sensor for receiving and storing in the associated memory an electrical signal corresponding to any light emitted by a reaction product acid configured to produce a graphic and/or data display corresponding to the intensity of the light emission.

2. The system of claim 1 in which the memory associated with the microprocessor includes a calibration database comprising a pre-calibrated data response factor to which the sample measurement data is applied or compared.

3. The system of claim 2 in which the stored pre-calibrated data response factor corresponds to the type of biocide.

4. The system of claim 2 in which the stored pre-calibrated data response factor corresponds to intensity of light emission of seawater containing 20 ppm of a compound containing a —CHO functional group.

5. The system of claim 2 in which the calibration batabase includes known concentrations of formaldehyde, acetaldehyde and glutaraldehyde.

6. The system of claim 2 in which the stored pre-calibrated data response factor corresponds to the configuration of components in the optical detection cell.

7. The system of claim 2 in which the stored pre-calibrated data response factor corresponds to the type of light sensor.

8. The system of claim 1 in which the microprocessor receives the electrical signal in real time.

9. The system of claim 1 in which the microprocessor is located at an off-site control center.

10. The system of claim 9 in which microprocessor is equipped with a transmitter and an antenna.

11. The system of claim 1 in which the buffering agent maintains the pH of the mixture at 4.5.

12. The system of claim 1 in which the buffer is selected from the group consisting of ammonium acetate and a mixture of potassium hydrogen phthalate and sodium hydroxide.

13. The system of claim 1 in which the flow cell comprises a closed circulation loop of predetermined volume, the loop including a chamber formed with a transparent wall, and a light source capable of emitting light of a predetermined wavelength selected to produce a visible fluorescence in an aldehyde-containing reaction product positioned proximate the transparent wall opposite the sensor.

14. The system of claim 13 in which the light sensor comprises a fiberoptic probe for receiving light emitted by any fluorescing reaction product and an optical detector comprising a sensor that is configured to produce a variable electrical signal that corresponds to the intensity of the fluorescence, the light sensor being isolated from the heated reaction mixture by the transparent wall.

15. The system of claim 14, wherein the light produced by the light source has a wavelength in the range of 380 nm to 480 nm.

16. The system of claim 14 in which the fiberoptic probe comprises a receptor end that is positioned opposite a flow line of the heated reaction mixture.

17. The system of claim 13 in which the transparent wall comprises a sheet or web of chemically-resistant transparent polymeric material.

18. The system of claim 1 in which the optical detection cell is constructed of polyether ether ketone (PEEK) or polytetrafluoroethylene (PTFE).

19. The system of claim 1 in which the heating vessel is configured to heat the reaction mixture to a temperature that is greater than the highest foreseeable ambient temperature of the environment which the system is located.

20. The system of claim 19 in which the heating vessel heats the reaction mixture to a temperature in the range of from 80° C. to 90° C.

21. The system of claim 1 in which the reagent storage vessel includes a sensor that produces a warning signal that is transmitted to the microprocessor and to operating personnel indicating a predetermined low level of reagent.

22. The system of claim 1 in which the sample metering pump, the reagent metering pump, or both are peristaltic pumps.

23. The system of claim 1 which includes a source of flushing liquid in valved fluid communication with the inlet of the sample metering pump for flushing the system after each test.

24. The system of claim 1 in which the flow cell includes a downstream outlet in fluid communication with a reaction mixture product storage chamber for storage of waste product flushed from the system.

25. The system of claim 1 which includes a solar-powered energy source and one or more storage batteries and associated circuitry to distribute electrical current to operate the system components.

* * * * *